United States Patent [19]

Giarretto

[11] Patent Number: 5,228,431
[45] Date of Patent: Jul. 20, 1993

[54] DRUG-FREE METHOD FOR TREATMENT OF THE SCALP FOR THERAPEUTIC PURPOSES

[76] Inventor: Ralph R. Giarretto, 3103 Lynde St., Oakland, Calif. 94601

[21] Appl. No.: 615,444

[22] Filed: Nov. 19, 1990

Related U.S. Application Data

[63] Continuation-in-part of Ser. No. 514,609, Apr. 26, 1990, abandoned.

[51] Int. Cl.⁵ ............................................. A61H 09/00
[52] U.S. Cl. ..................................... 128/24 R; 128/44
[58] Field of Search ................. 128/24 R, 36, 35, 34, 128/44, 62 R, 32, 39, 45, 46, 49, 24.2, 64, 54

[56] References Cited

U.S. PATENT DOCUMENTS

| | | | |
|---|---|---|---|
| 765,746 | 7/1904 | Miner | 604/315 X |
| 843,674 | 2/1907 | Funk | 604/315 X |
| 1,355,679 | 10/1920 | McConnell | 128/24 R |
| 2,232,254 | 2/1941 | Morgan | 128/45 |
| 2,338,339 | 1/1944 | La Mere et al. | 128/64 |
| 3,026,526 | 3/1962 | Montrose | 2/68 |
| 3,478,736 | 8/1967 | Roberts et al. | 128/36 |
| 3,481,326 | 12/1969 | Schamblin | 128/24.2 |
| 4,469,092 | 9/1984 | Marshall et al. | 128/36 |
| 4,765,316 | 8/1988 | Marshall | 128/36 |
| 4,836,192 | 6/1989 | Abbate | 128/38 |

OTHER PUBLICATIONS

Klemp, P. et al.: "Subcutaneous Blood Flow in Early Male Pattern", *Journal of Investigative Dermatology*, 92:725-726 (1989).

Lundvall, J. and Lanne, T.: "Transmission of Externally Applied Negative Pressure to the Underlying Tissue. A Study on the Upper Arm of man", *Acta Physiol. Scand.*, 136:403-409 (1989).

Maddin, S. et al.: "The Biological Effects of a Pulsed Electrostatic Field with Specific Reference to Hair", *International Journal of Dermatology*, 29:446-451 (1990).

Primary Examiner—Edgar S. Burr
Assistant Examiner—Eric P. Raciti
Attorney, Agent, or Firm—Hana H. Dolezalova

[57] ABSTRACT

A novel and improved drug-free treatment for alopecia, headache and other stress-induced diseases by stimulation using alternatively ambient and negative pressures. The treatment promotes hair growth by inducing alternatively an ambient pressure and a negative pressure stimulation to the bald or balding scalp. The treatment administered for several minutes daily for several weeks results in restoration of the hair growth, in the prevention of the hair loss and in the reduction of headaches.

11 Claims, 3 Drawing Sheets

DRUG-FREE METHOD FOR TREATMENT OF THE SCALP FOR THERAPEUTIC PURPOSES

This is a continuation-in-part application of the patent application Ser. No. 07/514,609 filed Apr. 26, 1990, now abandoned.

BACKGROUND OF INVENTION

1. Field of the Invention

This invention concerns a novel and improved drug-free treatment and prevention of alopecia and stress related diseases by using alternatively an ambient and a negative pressure. In particular, this invention concerns a treatment and prevention of alopecia by stimulating a hair growth by applying alternatively the ambient and negative pressure to the bald or balding scalp for several minutes once or several times a day. Headaches and other stress related diseases are treated and prevented in the same way by increasing the blood circulation to the affected areas. The stimulation is administered through a helmet connected to a vacuum means and equipped with a seal.

2. Background and Related Disclosures

Alopecia or baldness is a partial or complete loss of hair. Alopecia may result from genetic or nongenetic factors, from aging or from local or systemic disease and is very likely connected to stress and ravages of the force of gravity. Since the hair represents a symbol of youthfulness and virility, a social stigma and personal discomfort is often associated with balding.

Male pattern baldness is extremely common and it is believed that it is caused by and requires the presence of androgens. The male pattern type of alopecia may be fairly extensive. Female pattern alopecia is not infrequent but is usually confined to thinning of the hair and seldom ends with complete baldness.

Although many preparations, chemicals, diets, drugs or surgical treatments have been developed and proposed throughout the history, still there is no effective treatment available which would restore or stimulate the growth of the hair in balding person without patient's need to undergo lengthy and painful surgical hair transplant or using drugs which have severe side effects.

Many nonmedicinal hair restorers were tried containing vitamins, minerals, proteins, metals, enzymes and various medicinal treatments, as described below. These hair restorers are administered either systemically, orally or directly topically to a scalp or to the hair, and various concoctions were prepared containing one or more above listed ingredients alone or in combination with other "miraculous" substances.

In both cases of systemic or topical administrations, these treatments have invariably failed. That is so, first, because it is extremely unlikely that any treatment administered orally or otherwise systemically in fact reaches the hair follicles. Second, the topically administered treatment must cross a formidable barrier which the human skin provides against the penetration of any matter trying to enter the body through the skin. Thus, in order for any topically administered substance to penetrate the skin, to reach the depth of the hair follicle and to restore its function, such substance must be administered in a very high concentration and be formulated in a way which allows a passage through the skin barrier.

Medicinal treatments of alopecia include steroidal treatments, hormonal treatments and treatment with other drugs, such as recently discovered treatment with minoxidil, previously known cardiovascular drug.

A systemic corticosteroid treatment, which is often used to treat alopecia areata, a sudden hair loss in circumscribed areas, is accompanied by a variety of severe and undesirable secondary symptoms. The treatment with steroids cannot be justified merely for cosmetic reasons as it is invasive to the body's equilibrium. (*The Merck Manual*, 2281, 15th Edition (1987)). A systemic hormone treatment with female hormone estrogen has been shown to reverse male pattern alopecia in a limited way. However, the hair restorative effect of this treatment is uncertain particularly as it produces unacceptable side effects such as enlarged breasts in males, a lack of facial and body hair, and an elevated tone of voice. Another type of hormonal treatment of alopecia is an injection of female hormones, in dilute concentrations, directly into the scalp or, in alternative, rubbing the solution containing these hormones into a man's scalp. Similarly to other topically administered drugs and to the systemic steroidal treatments, such applications may improve hair growth but eventually they result in similar secondary side effects as described above.

Currently, the only known and effective drug treatment of alopecia is with a topically administered 3% solution of minoxidil, a potent anti-hypertensive drug. This treatment is not without problems. Following the treatment, high quantities of minoxidil in blood have been observed, causing some patients to experience the major side effects such as tachycardia, swelling and difficulty in breathing. Moreover, currently available topical minoxidil preparations are formulated in a mixture of alcohol and propylene glycol which formulation leaves unattractive film on the scalp. (PDR, 2184, 43rd Edition, (1989)).

Thus, it would be desirable to have available a drug-free treatment for alopecia which would eliminate all the above stated disadvantages or, in alternative, to have available a treatment which would allow a reduced dosage of the drug while achieving the desired result, i.e., the hair growth. Scalp massages are frequently recommended to the balding people under the premise that the massage helps to increase the flow of nutrients and oxygen to the hair follicles. Various gears have been developed to administer such massage to the scalp. Mostly, such devices are complicated, multi-component apparatuses which are expensive, hard to assemble, operate and disinfect. For example, U.S. Pat. No. 4,469,092 describes an electromechanical system for stimulating the human scalp. The system includes a rigid helmet with internal pad comprising stimulation members which directly contact the scalp of the patient. A vibration motor housed within the helmet mechanically vibrates the fingers of the pad. A vacuum means supposedly distributes vacuum in the helmet's interior during vibration to stimulate the scalp, however, no effective means for achieving the vacuum are disclosed. U.S. Pat. No. 4,765,316 improves the above system to make it portable so that both vibrator and the vacuum units are located within the helmet. A head vibrator unit is disclosed in the U.S. Pat. No. 3,763,853. U.S. Pat. Nos. 1,681,111, 4,566,137 and 4,287,613 generally describe cushioned helmets and hats. All the above described scalp stimulators and vibrators are heavy, complicated and costly equipments which generally require specially built-in electrical and mechanical means, such as special pads, vibrators and vacuum pumps.

The current invention provides easy, simple, cheap and uncomplicated method for treatment of alopecia by scalp suction stimulation performed by alternating an ambient and negative pressure. Moreover, the current invention is also useful for relieving stress-induced diseases such as headaches, particularly migraine and sinus headaches and other stress related conditions.

SUMMARY

One aspect of this invention is a method for a drug-free treatment of alopecia, headaches and other stress related diseases.

Another aspect of this invention is a method for a drug-free treatment of alopecia and headaches achieved by increasing blood circulation and blood flow through the scalp using alternate negative pressure, and ambient or positive pressure (air flow) to stimulate the scalp circulation and to augment a flow of bodily fluids to and from hair follicles.

Still another aspect of this invention is a method for a resuscitation of the blood circulation and a stimulation of bodily fluids flow achieved by specially modified helmet having seal means to seal off the space within the helmet to achieve, by using a vacuum source, an interior negative pressure between 10-85 mm Hg and having means for alternating the ambient pressure with the negative pressure.

Yet another aspect of this invention is a method for treatment of alopecia or headaches comprising a placing over the head of a patient a helmet connected to a vacuum source, creating a negative pressure in the interior of the helmet placed around the patient's head by inflating an inflatable seal that conforms to the variety of head shapes and sizes, or otherwise sealing the interior of the helmet, followed by a stimulation achieved by alternating 15 seconds to 3 minutes periods of the negative pressure stimulation and the period of relief at ambient or positive pressure.

Still another aspect of this invention is the above method comprising an optional enhancement of the stimulation with a scalp massage achieved by placing inside of the helmet a removable insert having soft or semisoft extrusions. When the helmet is positioned on the patient's head prior to the treatment, these extrusions are not intended to touch the patient's scalp but will, during the alternating negative and ambient pressure periods, move gently and in this way passively massage the scalp.

Still yet another aspect of this invention is any of the above treatments followed with topical administration of a solution containing a drug, medicament or any other active ingredient promoting hair growth or stimulating hair follicles.

DEFINITIONS

Figure 1:
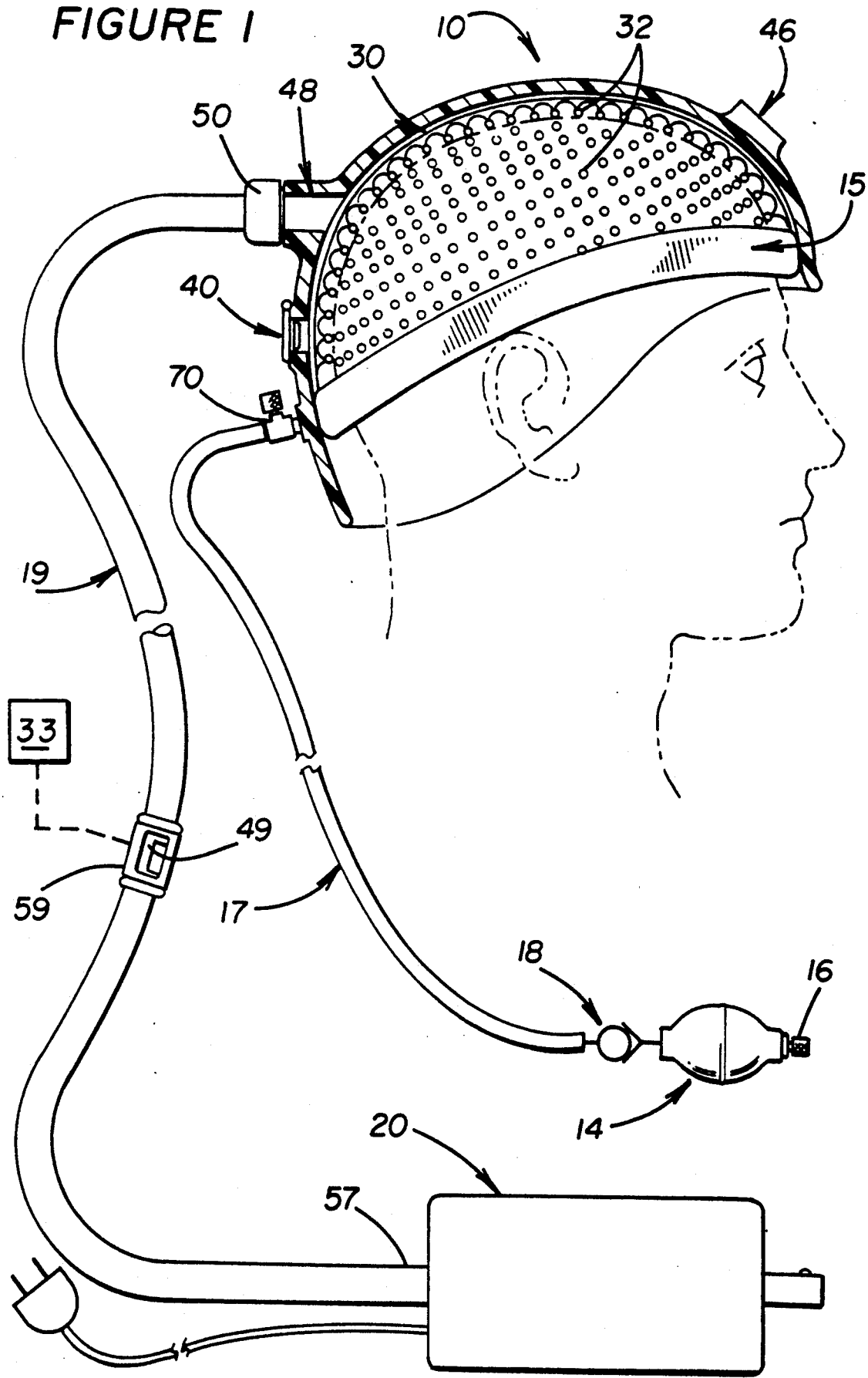
FIG. 1 depicts a system useful for treatment of alopecia, headaches and stress induced diseases.

As used herein:

"Vacuum" means a gas pressure below normal atmosphere pressure.

"Negative pressure" means vacuum between 0-85 mm Hg.

"Ambient pressure" means the pressure equal to a surrounding atmosphere.

"Positive pressure" means the ambient pressure enhanced by the blowing of the warm air into the helmet.

DETAILED DESCRIPTION OF THE INVENTION

This invention is based on findings that stimulation of the scalp by alternate negative and ambient/positive air pressures which may be consistent with warming and cooling of the scalp, promotes the hair growth, restores the hair health, prevents the development of hair loss and substantially decreases its progress. Moreover, it relieves headaches, particularly migraine or sinus headaches and other stress induced diseases and discomforts.

The stimulation is achieved by alternating the ambient and negative pressures. Both the ambient pressure and negative pressure are induced via a helmet apparatus connected to a vacuum source having means for alternating the negative and the ambient pressures.

The ambient pressure may be achieved by simply shutting off the vacuum source creating the negative pressure or it may be accompanied by actual blowing of the warm air on the scalp. The negative pressure is created by vacuum suction. The therapeutically effective limits of the negative pressure are between 10-85 mm Hg preferably between 20-60 mm Hg. The negative pressure tolerance has to be build with the treatment time so that at the beginning, the lower negative pressures, such as 10-20, will be used. These pressures will then be slowly increased to 10-20, 20-30, 30-40, 40-50, 50-60, etc., until the comfortable tolerance level is found for each individual patient. Tolerance level may be different for each patient but will generally be within 10-85 mm Hg, preferably between 40-60 mm Hg, of the negative pressure.

The current treatment will be particularly useful for treatment of alopecia and psychosomatic diseases such as high blood pressure, ulcers, diabetes, sinusitis and migraine headaches which have been shown to be stress related. It has now been discovered that negative pressure may be beneficial for treatment and prevention of alopecia and these other diseases as it increases a pressure gradient at the peripheral circulation.

It has been postulated in the medical field that the force of gravity can have a modifying effect on pressure gradient and flux of body fluids in relation to the blood flow and an ionic fluid diffusion through cell membranes. In fact, people who stand for long periods of time often experience edema in their lower extremities. The edema is caused by pooling of blood in capillaries of the lower extremities which pooling then causes stasis of the upper body, in particular most distal head region. Since the continuous undisrupted flow of blood providing oxygen and nutrition to cells is essential for their normal function, many bodily dysfunction may be explained by slow capillary circulation or by the blockage of the peripheral circulation, both of which interrupt the normal supply of the target cells with nutrients, ions and oxygen and also effect removal of metabolic waste products.

Following the gravity theory, it seems probable that the head, and particularly the scalp supplied only by the net of small peripheral capillaries, would be particularly susceptible to a stoppage or diminution of the flow of blood or other body fluids. Alopecia, balding of the scalp, thus would seem to be a natural result for the gravity phenomena. *Medical Physiology and Biophysics*, 685 (1961) W.B. Saunders Comp.

Consequently, the mechanical stimulation may augment the circulation in places most exposed to the force gravity, i.e., in the head region. It may also slow the sagging of facial skin as the negative pressure lifts the facial skin and scalp stimulating blood circulation and increasing a blood flow to the entire head. In this way, the stimulation may restore the normal function of cells localized in cutaneous and subcutaneous head tissues.

In testing this hypothesis, it has now been found that the balding may be slowed down, prevented, or reversed by providing a stimulation by the negative pressure to the scalp. Similarly, it has been found that the migraine or sinus headaches may be relieved without medication by applying a mild negative pressure.

Such stimulation effects skin layers (FIG. 3), such as epidermis (8), dermis (4) and subcutaneous cellular tissue (10) including subcutaneous blood circulation which also supplies hair follicles. It may also induce peripheral vasodilation in deeper tissues, such as in the vessels in the brain thus relieving the migraine headaches caused by vasospasm of the brain vessels.

In this respect this drug-free treatment of alopecia simulates the effect of minoxidil on the hair growth. However, while the minoxidil faces formidable skin barrier which it must cross in order to get to the subcutaneous cellular tissue where the hair follicles are situated, a current treatment achieves this without any medication.

Figure 3:
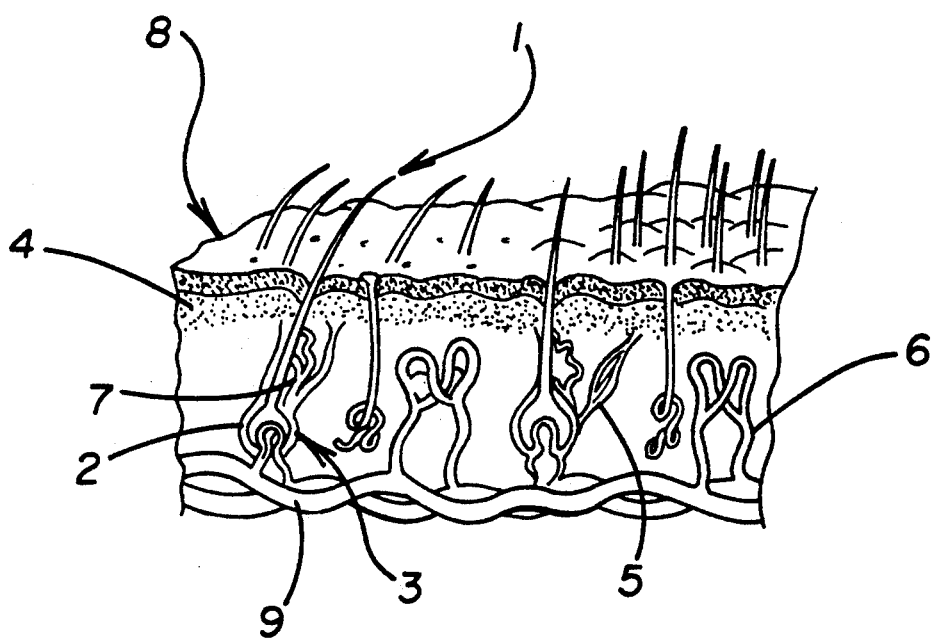
FIG. 3 shows anatomical cross section of the follicle with blood vessel supply.

The anatomical configuration of the hair as described in *Gray's Anatomy*, 1136 (1977) is shown in FIG. 3. FIG. 3, depicting a schematic anatomical cross-section of the scalp skin, shows that the hair (1) grows and is enveloped by the hair follicle (2), a follicular involution of the epidermis. Hair follicle has, at its bottom, a small conical vascular eminence called papilla (3) which is highly vascular. The follicular outer dermic coat is also highly vascular. Both the papilla (3) and dermis (4) have numerous minute nervous filaments (7) and extensive vascularization (6). Connected with the hair follicles are minute bundles of involuntary muscular fibers, arrectores pili (5), which are able to elevate the hair. It is clear that any deviation from the physiological status of the minuscule hair follicle (2), papilla (3) or muscle fibre (5) will have undesirable effect on the growth or regeneration of the hair. Thus, for example, slower circulation through the capillaries (6), insufficient supply of oxygen, ions or nutrients, muscle spasm caused by various psychosomatic stresses, or excessive supply of hormones may disturb, interrupt or completely stop hair growth and cause complete disruption of hair-follicle (2) function.

It is logical that the reversal of such deviation and the normalization of the physiological milieu may assist in restoration of the normal hair growth. An increased circulation to the skin and to the subcutaneous tissue enhances supply of nutrients, oxygen, ions, hormones and other endogenous compounds normally present in the blood. The increased circulation supplies these substances to the cells and at the same time enhances the removal of the waste material or other substances which are produced by the cells' metabolism in hair follicles. These waste materials, which accumulate in the follicles because there is an insufficient circulation to flux such materials away, may have detrimental and inhibitory effect on proper follicular function.

For example, it is currently believed that baldness is associated with the presence of 5-alpha reductase, an enzyme which is produced by the hair follicles and is often called a baldness enzyme. This enzyme combines with and converts testosterone, a male steroid hormone, into its derivative dihydrotestosterone. Dihydrotestosterone is known to cause some follicles to shrink. Since this process is continuous, it ultimately results in thinner and thinner hair, until the production of hair ceases altogether. At that time, the level of testosterone in hair follicles is low and the level of the 5-alpha reductase is high, and the process leading to baldness caused by dysfunctioning follicles is very progressive.

Such dysfunction of hair follicles is believed to be caused by the low levels of testosterone reaching the hair follicles. This is caused by decreased volume and slower flow of blood bringing testosterone and other nutrients and substances to the hair follicle. Thus, when the flood circulation to the follicles is decreased by stress or by forces of gravity, it logically follows that the level of testosterone, nutrients and other substances is also low. Consequently, if, as has been discussed above, the level of the 5-alpha reductase enzyme is high because it has not being removed sufficiently fast, most or all testosterone is quickly converted to dihydrotestosterone, which substance is known to cause the hair follicles to shrink and to stop or slow down their normal function. The normal function of testosterone, of which one effect is to promote the hair growth, is thus impaired. This whole process ends in the vicious circle where, since the blood circulation is slower, the removal of the 5-alpha reductase enzyme from the follicles is also slowed down and thus its concentration increases. The increased concentration of the enzyme makes it more available for conversion of already lower levels of testosterone. Low levels of testosterone, in turn, cause more follicles to shrink.

Consequently, when the blood circulation in the hair follicle is raised, the level of testosterone increases together with the level of oxygen, nutrients and ions necessary for healthy hair growth, and the level of the balding enzyme 5-alpha reductase, cellular metabolic waste, toxins, carbon dioxide, water, metabolic derivatives of testosterone and/or other hormones are decreased by the rapid removal of these substance due to the increased rate of the circulation.

Moreover, the increased rate of circulation also increases a pressure gradient between blood capillaries and cells thus further augmenting exchange of various materials between blood and cells and vice versa.

The primary therapeutic efficacy of this invention depends on increasing the blood circulation in the target tissue, on increasing the diffusion exchange of nutrients, ions, oxygen and hormones between the blood and cells of the hair follicle and on the faster removal of waste materials from the hair follicle cells by the negative pressure stimulation.

The effect of the current treatment on the sinus or migraine headache is the same. By increasing the blood circulation in the brain tissue, the nutrients and oxygen are brought in and the substances causing the spasm or pain are washed away.

In practice of the current invention, the patient who is bald, balding or has thin hair, or the patient who suffers from sinusitis or migraine headache or who is otherwise in need of such treatment is undergoing a daily negative pressure stimulation treatment.

The negative pressure stimulation is administered through a specially designed system comprising lightweight, rigid helmet equipped with or connected to a vacuum source, and the means to induce the vacuum inside of the helmet when the helmet is placed on a patient's head.

In its simplest form the helmet may be connected to a typical home type vacuum cleaner or to any kind of vacuum source suitable for this application.

In such a case, the helmet is equipped with pressure gauge by which the patient manually regulates the degree of the negative pressure.

The helmet, equipped with the inflatable seal or other sealing means, or shaped in such a way that it adheres to the patient's head, is placed around the head of the patient. The internal vacuum inside the helmet is achieved by the patient, who inflates the inflatable seal to such a degree that the helmet is completely sealed around his head.

The connecting hose between the helmet and the vacuum source is further equipped with a manometer, preferably with the mercury manometer or gauge which has lower negative pressure limitation equal to 10 mm Hg and the upper negative pressure limitation equal to 85 mm Hg. The scale is marked in such a way that the pressure exceeding 60 mm Hg, which is considered safe and optimal upper limit for negative pressure utilized by the method of this invention, is marked in red. There is a safety valve present in the system which releases vacuum should it exceed 85 mm Hg.

Figure 2:
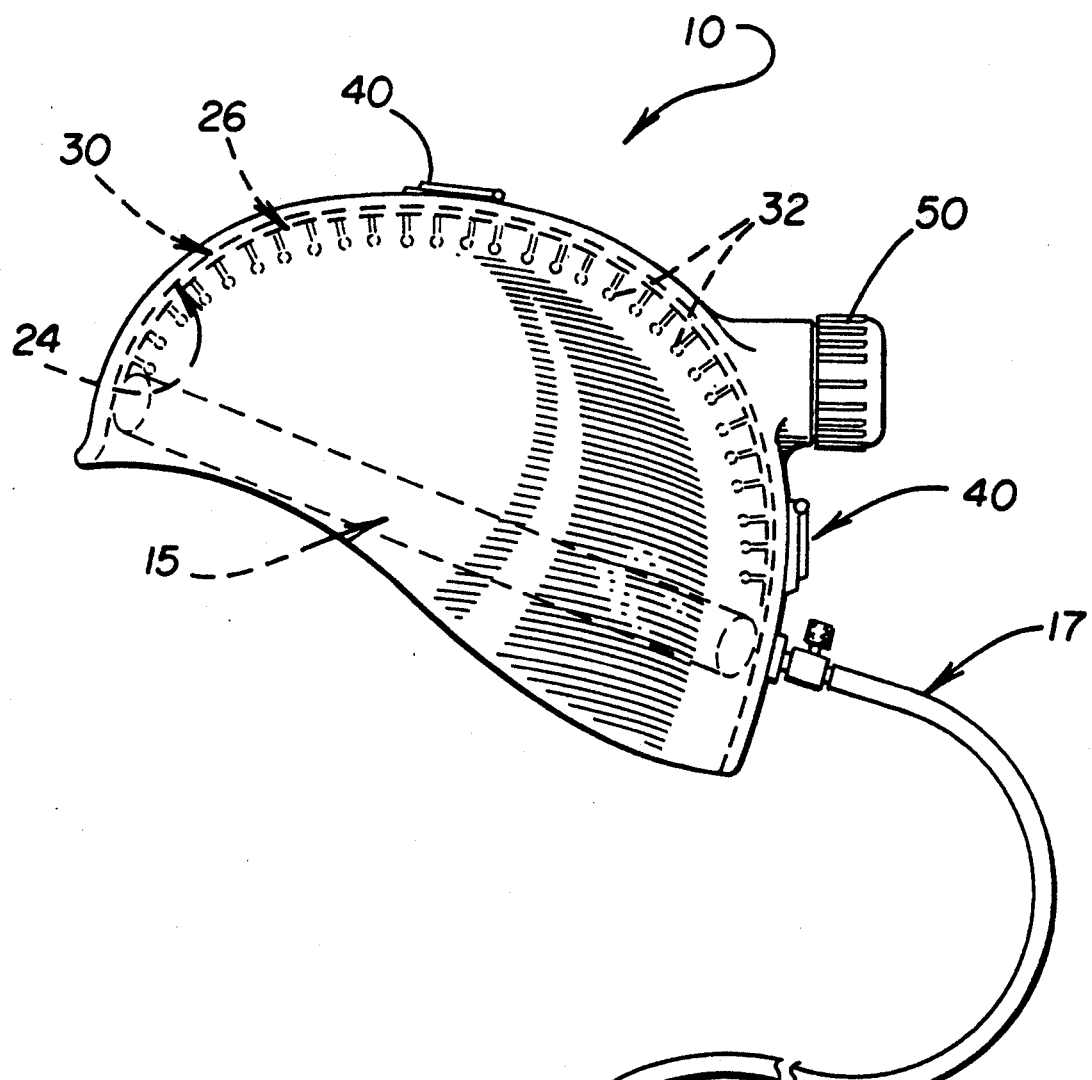
FIG. 2 is the cross section side-view of the helmet.

The stimulation is achieved by alternating negative and ambient pressures in the sealed off space between the helmet and patient's head wherein the vacuum is created by means of the unique expandable rubber seal (15) shown in FIGS. 1 and 2. The seal is adhered to the inside peripheral edge of the helmet (10) and during the treatment is inflated comfortably around the head to seal off the space. This expandable seal is a salient feature of one embodiment of this disclosure as it provides a seal around the head regardless its shape and size. Without the seal a negative pressure could not be achieved.

In another embodiment of the helmet, the helmet has a "derby" shape which has, around its edge, the U shaped soft rubber or plastic extrusion. The extrusion slides around the edge of the plastic helmet, in a flap-like fashion. When the "derby" helmet is placed over the patient's, and the vacuum source is switched on, the rubber or plastic flap seals the helmet around the patient's head. In this embodiment, no gluing or other attachment of the seal to the helmet is necessary. The U shaped rubber or plastic extrusion is fully exchangeable and thus much more hygienic than the inflatable seal.

The system used for the treatment of the current invention is shown in FIGS. 1 and 2. During the administration of the treatment, the patient is seated comfortably in a chair or on a supine recliner and the plastic helmet 10 is placed over the patient's head. Prior the placing of the helmet on the head, a clean paper band or thin perforated paper cap may be placed over the head. An expandable, inflatable seal 15 adherent to the inside surface of the helmet 10 is inflated by the patient or by the attendant by means of a rubber bulb, such as found on a standard mercury manometer, to achieve complete seal between the helmet and the patient's head. The internal pressure of inflatable seal is usually between 100-250 mm Hg depending on the patient comfort. In the second "derby" helmet embodiment, the helmet is simply positioned over the head.

The seal of the helmet may be a tube made of rubber plastic or other suitable material which can be inflated or it can be a simple flap, such as a loose flap made of plastic material such as PVC, vinyl, nylon or rubber which may optionally have pull string. During the negative pressure treatment, the flap or the seal which is attached to the inside of the helmet and surrounds the patient's head is slowly drawn around the patient's head to seal off the inside of the helmet 10 as a negative pressure is created by means of vacuum.

The helmet's outlet 48 connects the inside of the helmet with the outside. The outlet 48 is connected via a connector 50 to a flexible hose 19 connected to a suction pump or vacuum source unit 20. Any type of commercially available vacuum source may be advantageously utilized as well as vacuum source units specially built for this purpose. It is one of the advantages of this invention that for the home use, a conventional home vacuum cleaner may be used as a vacuum source.

For use of the home vacuum cleaner, the degree of the negative pressure and alternation of the negative and ambient pressure may be achieved by a window 49 in the hose 19, which window 49 is covered with the closely fitting turnable sleeve 59. The sleeve 59 has a slit-like opening which when the sleeve is turned around the hose 19 may completely close the window 49 to achieve complete vacuum, open the window completely to achieve the ambient pressure or to open window 49 only partially to let in certain amount of the air in order to ease the degree of the negative pressure. In this way, the degree of the negative pressure applied to the scalp and the scalp stimulation are very simply regulated.

For specially designed system according to the current invention, the vacuum unit, is build-in together with a mercury manometer and timer allowing the alternating pressures to be done manually or automatically via spring loaded alternating flap valve placed on the hose section.

In one embodiment of this method, the treatment will be achieved by simply alternating the negative pressure applied for certain period of time with the induction of the ambient pressure simply by switching the vacuum source on and off.

In another embodiment, the vacuum source will have an alternating means able to create the negative pressure and also to provide a blowing of the air, i.e., the positive pressure.

In the third embodiment, the vacuum source will have all three capabilities, i.e., to crate the negative pressure, to create the ambient pressure and to create the positive pressure.

The vacuum source unit 20 is then started, preferably first to administer the ambient or the positive pressure which may be accompanied by blowing a preferably lukewarm air on the scalp. After blowing the warm air on the scalp for about 5 seconds to 5 minutes, preferably around 30 seconds to 1 minute, the negative pressure is initiated between 10-85 mm Hg, preferably between 40-60 mm Hg applied to the patient scalp for about 5 seconds to 10 minutes, preferably for about three minutes. The degree of the negative pressure is regulated automatically, manually or by the opening and closing of window 49 on the hose 19, as described above. The alternating process is repeated 1-10 times or more, depending on patient's comfort. During the treatment, patients scalp becomes red and warm, oily and often sweaty. The blood circulation and the gas, water, nutrient exchange between the blood and cells by increased diffusion are raised substantially as is also the waste material removal. Following usually about two weeks of treatment, the first signs of fuzzy hair appear in the area submitted to the ambient/negative pressure. Visible thin hair appear in about three weeks of daily treatment. The treatment is repeated preferably daily but at least three times a week, one to several times a day, for as long as needs be. The results will depend on the number of treatments.

The distinct advantage of this invention is that while the more complicated equipment with predetermined pressure, predetermined alternating times and predetermined temperature of the blowing air or ambient temperature will be generally available in hair or cosmetic salons, the helmet part which is simple and inexpensive, can be purchased separately and advantageously utilize the home vacuum cleaner as a source of vacuum. In such an instance, the window 49 on the hose 19, having the plastic sleeve ring 59, and the inflatable seal 15 in the helmet may be opened or closed by the patient directly and consequently, the patient may control the timing and degree of the negative pressure, and the compression of the expandable seal 15 around his head. The seal 15 in combination with the window 49 allows the regulation of the degree of negative pressure achieved at the scalp and the amount of lifting action on the scalp according to the patient's comfort.

Alternation of ambient and negative pressures within the sealed helmet stimulates the skin function and the function of the hair follicles. The negative pressure serves to lift the scalp and raise the hair shaft to overcome the force of gravity and increases the space between the skull and scalp, thus allowing more free flow of fluids and decompression of the hair follicle. Since the negative pressure sometimes makes the scalp feel cold, the blowing of the warm air, or applying of warm compresses on the scalp may help the scalp to warm up, open the sweat and hair pores, dilate and relax peripheral circulation, and generally even more improving the blood circulation to and from the follicles. Therefore, it is not necessary but preferable, to blow a warm air on the scalp. The increased blood circulation provides the hair follicles with increased supply of oxygen and nutrients and helps the hair follicles regeneration and the regeneration of their function. With this treatment, the function of completely dysfunctional follicles may be restored to the normal state.

The negative pressure increases diffusion of oxygen and nutrients into the hair follicle from the follicular artery. As seen in FIG. 3, the artery 9 is physically positioned within the follicle in close contact with the follicles papilla 3. During the negative pressure stimulation, the dilated blood vessel (9) is able to transfer more oxygen and nutrients to the follicle and, due to an increased rate of the diffusion, these nutrients and oxygen will diffuse faster and in larger amounts. Moreover, the follicle itself is cleansed and stimulated during the negative pressure by removal of all accumulated impurities and sebum in the follicle and in the hair shaft. The negative pressure further stimulates the transport of oxygen and nutrients within the hair shaft, enhances keratinization, hair growth, restores the hair strength and color. The negative pressure further pulls the facial and scalp skin up slightly which allows a restoration of fat cells and fibrous tissue located in dermis 4, it improves a function of sebaceous glands which oils the hair, and it relaxes the hair-erecting muscles arrectores pili 5. By alternating a relaxation period during the administration of positive or ambient pressures with the administration of the negative pressure, the hair follicles metabolism becomes stimulated and in the presence of increased supply of oxygen and nutrients, the hair growth is restored, enhanced or initiated.

In another aspect of this invention, the above treatment is combined with hair growth drug promoting treatment. In practice, the negative pressure stimulation treatment is performed as described above. Immediately after the termination of the treatment, a weak solution of any hair growth stimulating compound, such as minoxidil in amount about 0.01-3%, in alcohol, preferably formulated in propylglycol or in liposomes is applied to the previously stimulated scalp. Other drugs, vitamins, hair growth promoters, follicle washes, follicle nutrients and such others are similarly applied following the negative pressure stimulation treatment.

In another aspect of this invention, the stimulation may be further enhanced with a scalp massage. The scalp massage is achieved by inserting into the helmet 10 an insert 30 and attaching it adhesively to the helmet's inner surface 24 as shown in FIG. 2. The insert 30 has semirigid or soft, hair-like, or brush-like extrusions 32 or bristles 32. When the helmet is positioned on the patient's head, the extrusions 32 may or may not be touching the scalp. During the negative pressure phase, or during the periods of ambient pressure these extrusions move gently thus passively extenuating the effect of warming or the negative pressure of the scalp. This aspect may be further followed and combined with drug treatment, as described above.

A system used for negative pressure stimulation is shown schematically in FIG. 1. The helmet 10 is firmly positioned over the patient's head. The helmet 10 is made of light-weight but rigid plastic or metal material and may be either secured on the stand, attached to the wall or freely movable. The inflatable seal 15 which is unremovable part of the helmet 10, is made of the inflatable material such as a plastic on rubber hose or is in the form of the U shaped flap (not shown in the drawing) or the plastic U shaped extrusion. The seal 15 is soft and deforms according to the shape of the patient's head so that it seals the outside from the inside of the helmet and allows a creation of the negative pressure inside of the helmet. The seal is connected through valve stem 70 with a tube 17 to a bulb 14 which has a screw 16 to effect inflating the seal by pumping the air into it to achieve an inner seal pressure around 100-250 mm Hg. Between tube 17 and bulb 14 is the check and release valve 18 which automatically releases the air if the seal becomes for any reason overinflated. The helmet 10 has an opening outlet 48 which is terminated with connector 50. Connector 50 is of such a size and dimensions which fit tightly around a hose 19 connecting it to the vacuum source unit 20. Connector 50 is able to make sealable connection with the hose 19. The vacuum source unit may be any Commercially available pump or any other equipment suitable for such purposes and would preferably be portable and silent.

In the newer system, the hose 19 is connected to the panel equipped with a timer and a gauge for predetermination of the period of administration of the negative and ambient or positive pressure and the degree of the negative pressure. Thus, for example, the gauge and the times may be preset to apply the negative pressure of 30 mm Hg for 3 minutes, alternated with 30 seconds of the ambient pressure. Or, the negative pressure of 60 mm Hg may be applied for 30 second alternating with blowing of warm air (positive pressure) for 3 minutes. All these parameters are freely interchangeable and would depend entirely on the patient comfort and desire.

The helmet 10 has further optionally one or more built-in valves 40 which are flap-like and can open automatically during the blowing period if the blowing extends certain pressure. These flaps are closed and sealed during the vacuum period. The flaps are made of strong rubber or plastic.

One variation of the above helmet 10 described in FIG. 1 is the helmet 10 having the second outlet 46 to which the hair blower (not shown) can be sealably attached. This variation would allow the use of the vacuum cleaner as a source of the vacuum and the hair blower as the source of the positive pressure.

Optionally, the helmet 10 may be lined up with an insert 30 which has a plurality of stand-off pins, bristles, brushes, extrusions or some such structures 32 which will further stimulate the surface of the scalp. The insert 30 is removably attached to the bottom of the helmet 24 and has a variable shape. It may have a shape of the top of the head, if the top of the head is to be massaged. If, on the other hand, the massage is to be introduced only to a single or multiple bald patches, the insert has a pattern similar to patches to be massaged. Similarly, when the crown is to be massaged, the insert with extrusions will have a crown shape. The inside of the helmet 10 is the lining 26 which is soft and nonirritating to the scalp. The lining 26 may be exchanged after each use for hygienic reasons or may be covered by exchangeable kerchief or, as described above, by exchangeable insert.

These and other aspects of this invention are contemplated to be included within the scope of the current invention.

UTILITY

The primary use of the current invention is for treatment of the alopecia and for relief from stress induced diseases, or sinus and migraine headaches when the negative pressure provides a stimulation of the blood circulation. However, other non-drug therapeutic uses, such as for relief of head spasms caused by peripheral constriction of the head circulation, or high blood pressure are also possible.

The primary target for this treatment is the bald or balding patient. With several minutes treatment/day according to this invention the patient, without administration of any drug or in combination with a much smaller amount of hair growth promoting drug, the patient's hair growth may be restored.

EXAMPLE 1

Treatment of Baldness

This example illustrates the method for treatment of baldness by stimulating a patient's scalp with alternating ambient and negative pressures. Group of 10 bald or almost bald men were treated.

Each patient was seated in a comfortable chair and the paper strip was placed around his head similarly to a sweatband. The helmet having the rubber inflatable seal attached to its edge was placed over his head and the patient was instructed to pump the air into the seal until the seal was tightly enclosing the paper sweatband and effectively sealing the helmet's inner space around the patient's head. Patient was instructed to control the tightness of the seal so that it felt comfortable. The helmet was attached with a rubber hose to a panel containing a vacuum source unit of 3 hp, a mercury manometer with a dial for control adjustment and manipulation of the negative pressure, and a timer having a capability for manual or automatic alternating of the negative and ambient or positive pressure. The panel was connected to the electrical outlet. At the beginning of the treatment, the manometer dial was slowly turned so that the negative pressure gradually increased until the full vacuum of about 20–30 Hg was achieved. The negative pressure was slowly increased with every subsequent treatment until the upper limit 60 mm Hg was reached. The patient was treated from 3 minutes with the negative pressure depending on his reported comfort or discomfort. Then, the negative pressure was interrupted and the patient was treated at ambient pressure for periods from 10–30 seconds. The periods of negative pressure stimulation alternated with periods of ambient pressure. The period of ambient pressure was always shorter. After about 3–7 minutes of treatment (i.e., usually 3 alternations) depending on the patient's comfort, the helmet was removed and the scalp was examined for cleanliness, sweat, scratches, and irritations. The color of the scalp was usually bright red, warm, oily and moistured. The hair, if there were any prior to treatment seemed to get more luster and were visually refreshed. The treatment regimen was followed every day 3–7 days a week, except that the negative pressure was gradually increasing to the level comfortable to individual patient but preferably no more than to 60 mm Hg. After two weeks, or after about 6–10 treatments, the first signs of patchy gentle fluff appeared in bald patients. With extended treatment, after about three weeks of several treatments a week, the fluff changed to thin hair.

EXAMPLE 2

Pulsating Treatment of Alopecia by Negative/Ambient Pressure Stimulation

This example illustrates the method for treatment of alopecia by alternating ambient and negative pressure stimulation in rapid succession by pulsation. Group of 10 bald or almost bald men were treated.

Each patient was seated in a comfortable chair and the "derby" helmet having the plastic U-shaped flap around its edge, was placed over the patient's head. When the vacuum was initiated, the flap closed around the patient's head and effectively sealed the helmet's inner space around the patient's head, as described above, the helmet was connected to the panel containing a vacuum source, a manometer, a dial and a timer. The dial for setting-up the negative pressure was set-up at the pressure comfortable to the patient. The timer was set up to switch on and off to apply the negative pressure in about 5–30 seconds intervals. The negative pressure was quickly alternated with ambient pressure. The patient was treated from 3–10 minutes with alternating negative, and ambient pressure depending on his reported comfort or discomfort. In this treatment regimen, the periods of negative pressure alternated with periods of ambient pressure were equal, usually 30 seconds of each. After about 3–10 minutes of treatment, depending on the patient's comfort, the helmet was removed and the scalp was examined for cleanliness, sweat, irritations and scratches. The color of the scalp was usually reddish, warm, oily and moistured. The treatment was followed every day 3-7 days a week. This treatment was not as effective as the treatment of Example 1. After about two-three weeks, approximately after 15 treatments, the first signs of patchy soft fluff appeared. With continued treatment, the fluff changed to thin hair after about four weeks of therapy. In patients having thin hair prior to the beginning of treatment, hair looked healthier, stronger and thicker after the two-three weeks of treatment.

EXAMPLE 3

Treatment of Migraine Headache with Alternating Pressure Stimulation

This example illustrates the relief from a migraine headache using the treatment regimen of this invention.

A patient was in a supine position. The "derby" helmet having the plastic U-shaped flap around its edge, was placed over the patient's head. When the vacuum was initiated, the flap closed around the patient's head and effectively sealed the helmet's inner space around the patient's head. As above, the helmet was connected to the panel containing a vacuum source, a manometer, a dial and a timer. The dial for setting-up the negative pressure was set-up at the pressure between 10-20 mm Hg, in any case, at the pressure comfortable to the patient. The timer was set up to switch on and off to apply the negative pressure in about 5-20 seconds intervals. The negative pressure was quickly alternated with ambient pressure. The patient was treated from 3-30 minutes with alternating negative, and ambient pressure depending on his reported comfort or discomfort. In this treatment regimen, the periods of negative pressure alternated with periods of ambient pressure were equal, usually 30 seconds of each. After about 3-10 minutes of treatment, the helmet was removed.

One patient who received about 30 minutes of this treatment of alternating mild 20-30 mm Hg negative pressure with the ambient pressure, experienced complete relief from the persistent migraine, which usually lasted the whole day. After the treatment, the patient's ocular pressures and pain substantially receded or stopped completely. The treatment was induced at any time when the migraine headaches reappeared which, in this particular patient, could be as many as 2-3 times a week. The patient was simultaneously taught relaxation techniques.

What is claimed is:

1. A method for treatment of the scalp for therapeutic purposes comprising the steps of:
    (a) placing a helmet over the head of a patient;
    (b) sealing the helmet to a substantially air-tight degree to seal off the inner space of the helmet between the helmet and the patient's head;
    (c) connecting the helmet to a vacuum source, and;
    (d) applying alternating negative and ambient pressure to the inner space of the helmet for 1 to 30 minutes.

2. The method of claim 1 wherein the sealing of the helmet is accomplished with a rubber seal.

3. The method of claim 2 wherein the rubber seal is inflatable.

4. The method of claim 3 wherein the sealing of the inner space of the helmet is achieved by inflating the rubber seal.

5. The method of claim 4 wherein the treatment is administered daily.

6. The method of claim 5 wherein the treatment is administered for 5 to 15 minutes.

7. The method of claim 6 wherein the negative pressure is between 10-60 mm/Hg.

8. The method of claim 7 wherein the negative pressure is administered for 1 to 10 minutes and the ambient pressure is administered for one second to five minutes.

9. The method of claim 8 wherein the pressure alternates between negative pressure administered for 2 to 3 minutes and ambient pressure administered for 30 to 60 seconds.

10. The method of claim 8 wherein the negative pressure is between 30-60 mm/Hg.

11. The method of claim 8 wherein the negative pressure is between 10-30 mmHg.

* * * * *